United States Patent
Kyal et al.

(10) Patent No.: US 9,504,426 B2
(45) Date of Patent: *Nov. 29, 2016

(54) USING AN ADAPTIVE BAND-PASS FILTER TO COMPENSATE FOR MOTION INDUCED ARTIFACTS IN A PHYSIOLOGICAL SIGNAL EXTRACTED FROM VIDEO

(71) Applicant: Xerox Corporation, Norwalk, CT (US)

(72) Inventors: Survi Kyal, Rochester, NY (US); Lalit Keshav Mestha, Fairport, NY (US)

(73) Assignee: Xerox Corporation, Norwalk, CT (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/099,358

(22) Filed: Dec. 6, 2013

(65) Prior Publication Data

US 2015/0157270 A1    Jun. 11, 2015

(51) Int. Cl.
| | |
|---|---|
| *A61B 5/00* | (2006.01) |
| *A61B 5/024* | (2006.01) |
| *A61B 5/113* | (2006.01) |
| *A61B 5/11* | (2006.01) |

(52) U.S. Cl.
CPC ............ *A61B 5/7207* (2013.01); *A61B 5/024* (2013.01); *A61B 5/1128* (2013.01); *A61B 5/1135* (2013.01); *A61B 5/7203* (2013.01); *A61B 5/7278* (2013.01); *A61B 2576/00* (2013.01)

(58) Field of Classification Search
None
See application file for complete search history.

(56) References Cited

U.S. PATENT DOCUMENTS

| | | | |
|---|---|---|---|
| 2003/0009091 A1* | 1/2003 | Edgar et al. | 600/323 |
| 2003/0187341 A1* | 10/2003 | Sackner | A61B 5/0205 600/388 |
| 2011/0251493 A1* | 10/2011 | Poh et al. | 600/477 |

OTHER PUBLICATIONS

Yu Sun et al. "Motion-compensated noncontact imaging photoplethysmography to monitor cardiorespiratory status during exercise", Journal of Biomedical Optics, Jul. 2011, vol. 16 (7).*
Poh et al. "Non-contact, automated cardiac pulse measurements using video imaging and blind source separation", Optical Express, May 2010, vol. 18, No. 10 , pp. 10762-10774.*
Cennini et al. "Heart rate monitoring via remote photoplethysmography with motion artifacts reduction", Optical Express, 2010, vol. 18, No. 5, pp. 4867-75).*

(Continued)

*Primary Examiner* — Katherine Fernandez
*Assistant Examiner* — Marjan Saboktakin
(74) *Attorney, Agent, or Firm* — Philip E. Blair; Fleit Gibbons Gutman Bongini & Bianco P.L.

(57) ABSTRACT

What is disclosed is a system and method for compensating for motion induced artifacts in physiological signals extracted from a video of a subject being monitored for a physiological function in a non-contact, remote sensing environment. The present method identifies a center frequency from a physiological signal obtained from processing a prior video segment. Since a moment to moment change in pulse frequency from one video segment to a next is not very large, signals obtained from sequential video segments can be repeatedly processed and an adaptive band-pass filter repeatedly re-configured and used to filter a next video segment, and so on. Using the teachings disclosed herein, a motion-compensated continuous cardiac signal can be obtained for the subject for continuous monitoring of the subject's cardiac function via video imaging. The teachings hereof provide an effective means for compensating for movement by the subject during video acquisition. Various embodiments are disclosed.

24 Claims, 8 Drawing Sheets

(56) References Cited

OTHER PUBLICATIONS

Liu et al., "Method and Systems for Vascular Pattern Localization Using Temporal Features", U.S. Appl. No. 13/710,794.

Mestha et al., "Removing Environment Factors From Signals Generated From Video Images Captured for Biomedical Measurements", U.S. Appl. No. 13/401,207, filed Feb. 21, 2012.

Xu et al., "Monitoring Respiration With a Thermal Imaging System", U.S. Appl. No. 13/103,406, filed May 9, 2011.

Xu et al., "Subcutaneous Vein Pattern Detection Via Multi-Spectral IR Imaging in an Identity Verification System", U.S. Appl. No. 13/087,850, filed Apr. 15, 2011.

Mestha et al., "Deriving Arterial Pulse Transit Time From a Source Video Image", U.S. Appl. No. 13/401,286, filed Feb. 21, 2012.

Mestha, et al., "Estimating Cardiac Pulse Recovery From Multi-Channel Source Data Via Constrained Source Separation", U.S. Appl. No. 13/247,683, filed Sep. 28, 2011.

Mestha et al., "Systems and Methods for Non-Contact Heart Rate Sensing", U.S. Appl. No. 13/247,575, filed Sep. 28, 2011.

Mestha et al., "Video-Based Estimation of Heart Rate Variability", U.S. Appl. No. 13/532,057, filed Jun. 25, 2012.

Kyal et al., "Continuous Cardiac Signal Generation From a Video of a Subject Being Monitored for Cardiac Function", U.S. Appl. No. 13/871,766, filed Apr. 26, 2013.

Mestha et al., "Processing a Video for Respiration Rate Estimation", U.S. Appl. No. 13/529,648, filed Jun. 21, 2012.

Mestha et al., "Processing a Video for Vascular Pattern Detection and Cardiac Function Analysis", U.S. Appl. No. 13/483,992, filed May 30, 2012.

Bernal et al., "Processing a Video for Tidal Chest Volume Estimation", U.S. Appl. No. 13/486,637, filed Jun. 1, 2012.

Kyal et al., "Continuous Cardiac Pulse Rate Estimation From Multi-Channel Source Video Data With Mid-Point Stitching", U.S. Appl. No. 13/871,728, filed Apr. 26, 2013.

Mestha et al., "Filtering Source Video Data Via Independent Component Selection", U.S. Appl. No. 13/281,975, filed Nov. 8, 2011.

Bernal et al., "Respiratory Function Estimation From a 2D Monocular Video", U.S. Appl. No. 13/680,838, filed Nov. 19, 2012.

Wang et al., "Multi-Band Infrared Camera System Optimized for Skin Detection", U.S. Appl. No. 13/416,436, filed Mar. 9, 2012.

Bernal et al., "Minute Ventilation Estimation Based on Depth Maps", U.S. Appl. No. 13/486,682, filed Jun. 1, 2012.

Bernal et al., "Minute Ventilation Estimation Based on Chest Volume", U.S. Appl. No. 131486,715, filed Jun. 1, 2012.

Kyal et al., "Continuous Cardiac Pulse Rate Estimation From Multi-Channel Source Video Data", U.S. Appl. No. 13/528,307, filed Jun. 20, 2012.

Mestha et al., "Determining Cardiac Arrhythmia From a Video of a Subject Being Monitored for Cardiac Function", U.S. Appl. No. 13/532,128, filed Jun. 25, 2012.

Tanaka et al., "Processing Source Video for Real-Time Enhancement of a Signal of Interest", U.S. Appl. No. 13/745,283, filed Jan. 18, 2013.

Xu et al., "A Video Acquisition System and Method for Monitoring a Subject for a Desired Physiological Function", U.S. Appl. No. 13/921,939, filed Jun. 19, 2013.

Xu et al., "Compensating for Motion Induced Artifacts in a Physiological Signal Extracted From a Single Video", U.S. Appl. No. 13/923,588, filed Jun. 21, 2013.

Xu et al., "Compensating for Motion Induced Artifacts in a Physiological Signal Extracted From Multiple Videos", U.S. Appl. No. 13/923,612, filed Jun. 21, 2013.

Piratla et al., "Web-Based System and Method for Video Analysis", U.S. Appl. No. 13/417,979, filed Mar. 12, 2012.

Wang et al., "Determining a Total Number of People in an IR Image Obtained Via an IR Imaging System", U.S. Appl. No. 12/967,775, filed Jun. 14, 2012.

Wang et al., "Determining a Number of Objects in an IR Image", U.S. Appl. No. 13/086,006, filed Apr. 13, 2011.

Wang et al., "Determining a Pixel Classification Threshold for Vehicle Occupancy Detection", U.S. Appl. No. 13/324,308, filed Dec. 13, 2011.

Mestha et al., "Method and Apparatus for Monitoring a Subject for Atrial Fibrillation", U.S. Appl. No. 13/937,740, filed Jul. 9, 2013.

Mestha et al., "Method and Apparatus for Monitoring a Subject for Fractional Blood Oxygen Saturation", U.S. Appl. No. 13/937,949, filed Jul. 9, 2013.

Mestha et al., "Method and Apparatus for Monitoring a Subject for Functional Blood Oxygen Saturation", U.S. Appl. No. 13/937,782, filed Jul. 9, 2013.

Mestha et al., "System and Method for Determining Video-Based Pulse Transit Time With Time-Series Signals", U.S. Appl. No. 14/026,739, filed Sep. 13, 201.

Mestha et al., "Generating a Flow-Volume Loop for Respiratory Function Assessment", U.S. Appl. No. 14/023,654, filed Sep. 11, 2013.

* cited by examiner

US 9,504,426 B2

USING AN ADAPTIVE BAND-PASS FILTER TO COMPENSATE FOR MOTION INDUCED ARTIFACTS IN A PHYSIOLOGICAL SIGNAL EXTRACTED FROM VIDEO

TECHNICAL FIELD

The present invention is directed to systems and methods for compensating for motion induced artifacts in physiological signals extracted from a video of a subject being monitored for a physiological function.

BACKGROUND

Monitoring of patient cardio-respiratory events is of vital clinical importance in the early detection of potentially fatal conditions. Current technologies that involve contact sensors require that the individual wears such devices constantly. Such a requirement can lead to discomfort, psychological dependence, loss of dignity, and may even cause additional medical issues such as skin infection when sensors have to be worn for an extended period of time. Elderly patients, infants, and those suffering from chronic medical conditions are more likely to suffer from such negative effects of continuous monitoring. The use of an unobtrusive, non-contact, imaging based monitoring of physiological events can go a long way towards alleviating some of these issues. Previous efforts have been directed to systems and methods which employ video image devices for monitoring a patient for a desired physiological function. In these methods, videos are captured of a region of interest of the resting patient and processed to estimate cardiac and respiratory functions from physiological signals extracted from time-series signals obtained from those videos. Xerox researchers have determined that movement by the resting patient such as turning the head, moving an arm, and the like, may impart or induce motion artifacts into the physiological signals extracted from video of that patient. The present application is directed to this issue.

Accordingly, what is needed in this art is a system and method for compensating for motion induced artifacts in physiological signals extracted from a video of a subject being monitored for a physiological function in a non-contact, remote sensing environment.

INCORPORATED REFERENCES

The following U.S. patents, U.S. patent applications, and Publications are incorporated herein in their entirety by reference.

U.S. patent application Ser. No. 13/923,588, "Compensating For Motion Induced Artifacts In A Physiological Signal Extracted From A Single Video", by Xu et al.

U.S. patent application Ser. No. 13/923,612, "Compensating For Motion Induced Artifacts In A Physiological Signal Extracted From Multiple Videos", by Xu et al.

BRIEF SUMMARY

What is disclosed is a system and method for compensating for motion induced artifacts in physiological signals extracted from a video of a subject being monitored for a physiological function in a non-contact, remote sensing environment. The present method utilizes prior knowledge of the pulse rate frequency obtained from having processed a previous video signal to filter the next motion-corrupted segment of video. Since the moment to moment change in the pulse frequency from one video segment to a next video segment is not very large, the clean signal obtained from the current batch has sufficient signal strength to adequately filter a next signal which has been corrupted due to motion. An adaptive band-pass filter is repeatedly re-configured and used to filter a signal obtained from a next sequential video segment in the captured video. In such a manner, continuous measurement of patient heart rate over time via video imaging is effectively enabled. The teachings hereof provide an effective means for compensating for movement by the subject during video acquisition.

In one embodiment, the present method involves performing the following. A video comprising a plurality of time-sequential image frames captured by a video imaging device is received. The video is of a subject being monitored for a desired physiological function. The image frames contain at least one area of exposed skin where a signal corresponding to the physiological function can be registered by the video imaging device. A first video segment $S_i$ in the received video is identified during which a movement by the subject is not likely to have induced motion artifacts in the video. Pixels in the image frames of the selected first video segment are processed to obtain a first time-series signal. A first physiological signal is extracted from the first time-series signal. The first physiological signal is analyzed to identify a first frequency of interest. A band-pass filter is created which has a center frequency corresponding to this frequency of interest with a pre-defined bandwidth. Thereafter, the following are repeated for all next sequential video segments $S_{i+1}$ in the video. (A) Pixels in image frames of this next video segment are processed to obtain a next time-series signal. (B) A next physiological signal is extracted from this next time-series signal. (C) The band-pass filter, which was created by having processed the previous video segment immediately prior to the current video segment, is used to filter the current time-series signal. This filtering produces a filtered current time-series signal. (D) A next physiological signal is then extracted from the filtered current time-series signal. (E) This physiological signal is analyzed to identify a next frequency of interest. (F) A next band-pass filter is generated or otherwise created which has a center frequency corresponding to this next frequency of interest. (G) This next band-pass filter is then used on a next iteration hereof. Steps (A-G) repeats until no more video segments remain to be processed. Thereafter, the sequential physiological signals are stitched together to generate a continuous physiological signal for the subject in which motion induced artifacts have been compensated for. The continuous physiological signal is then used to monitor the subject for the desired physiological function.

Features and advantages of the above-described system and method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for compensating for motion induced artifacts in physiological signals extracted from a video of a subject being monitored for a physiological function in a non-contact, remote sensing environment. The teachings hereof provide an effective means for compensating for movement by the subject during video acquisition.

Non-Limiting Definitions

Figure 1:
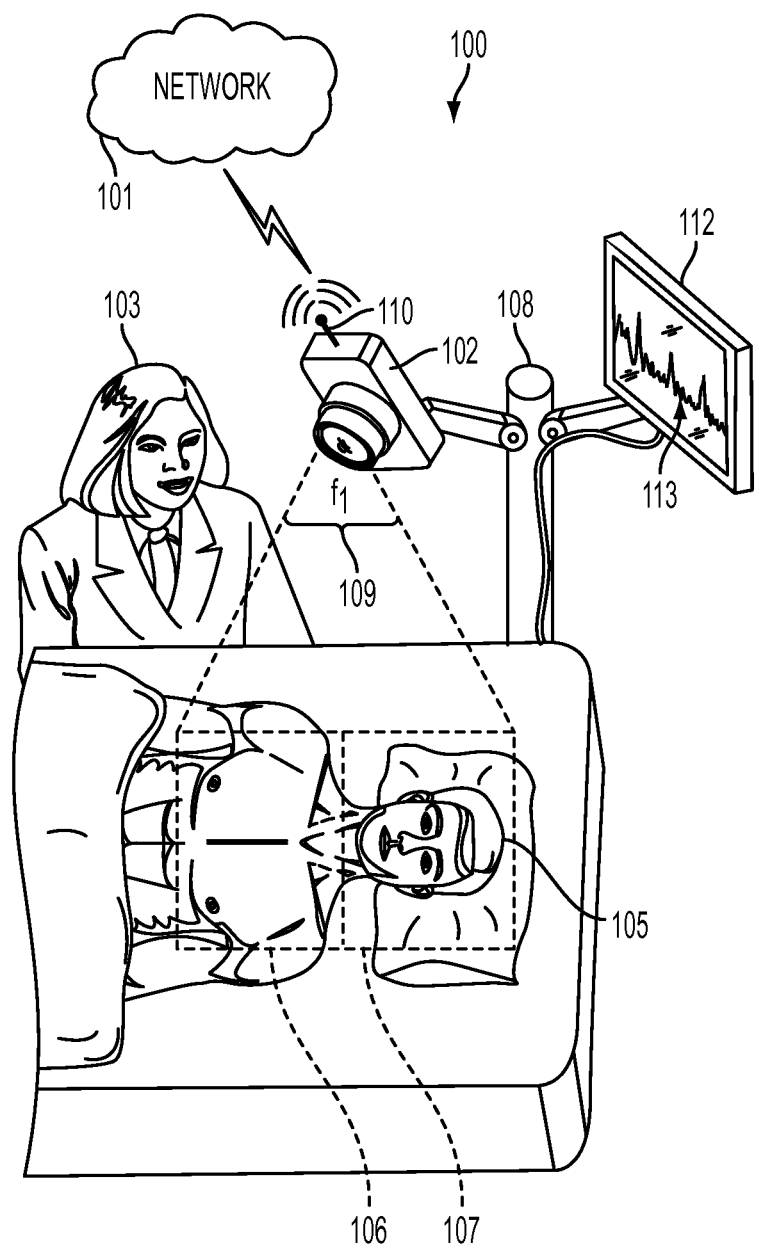
FIG. 1 shows a resting subject of interest being monitored for a desired physiological function in a in a non-contact, remote sensing environment.

A "subject of interest" refers to a living subject having a physiological function. Although the term "person" or "patient" may be used throughout this text, it should be appreciated that the subject may be something other than a human. Such terms are not to be viewed as limiting the scope of the appended claims strictly to human beings. FIG. 1 shows a resting subject of interest 105 being monitored for a desired physiological function in a non-contact, remote sensing environment.

A "video", as is generally understood, refers to a plurality of time-sequential image frames captured by a video imaging device of a subject being monitored for a desired physiological function. The image frames of the video are areas of exposed skin where a signal corresponding to the desired physiological function can be registered by the video imaging device. The video may also contain other components such as, audio, time, frame rate data, and the like.

A "video imaging device" refers to a single-channel or multi-channel video camera for acquiring a video of the subject. FIG. 1 shows an example video imaging device 102 capturing video of the resting patient 105. The video imaging device may be a device with a high frame rate and high spatial resolution such as, for example, a monochrome camera for capturing black/white video images, or a color camera for capturing color video images. The video imaging device may be a 3D imaging device or a device with thermal, infrared, multi-spectral or hyperspectral sensors. The video imaging device may comprise a hybrid device capable of operating in a conventional video mode with high frame rates and high spatial resolution, and a spectral mode with low frame rates but high spectral resolution. Video imaging devices comprising standard video equipment and those comprising specialized video sensors are readily available from a wide array of vendors in various streams of commerce. One such video imaging device is disclosed in: "Multi-Band Infrared Camera System Optimized For Skin Detection", U.S. patent application Ser. No. 13/416,436, by Wang et al., which is incorporated herein in its entirety by reference. A video imaging device may have a plurality of outputs from which the video can be retrieved or otherwise received on a per-channel basis and may incorporate memory, storage devices, and processors executing machine readable program instructions for processing and analyzing video in accordance with the teachings hereof.

"Receiving a video" is intended to be widely construed and includes: retrieving, receiving, capturing, acquiring, or otherwise obtaining video image frames for processing in accordance with the methods disclosed herein. For instance, the video can be retrieved from a memory or storage device of the video imaging device, or obtained from a remote device over a network. The video may be retrieved from a media such as a CDROM or DVD. The video may be downloaded from a web-based system which makes videos available for processing. One web-based system which makes videos available for processing is disclosed in U.S. Pat. No. 8,712,126 entitled: "Web-Based System And Method For Video Analysis", by Piratla et al. The video can also be retrieved using an application such as those which are widely available for handheld cellular devices and processed on the user's cellphone or other handheld computing device such as an iPad or tablet device. Video captured by a video imaging device is processed to isolate one or more region of interest.

An "area of exposed skin" refers to an unobstructed view of the skin of the subject as seen through a lens of the video imaging device used to capture video of that subject. FIG. 1 shows a first and second area of exposed skin 106 and 107, respectively, being captured by an example video imaging device. The image frames of the video are processed to isolate the one or more areas of exposed skin in each of the image frames of the video segments. Isolating an area of exposed skin in the image frames can be effectuated using a wide array of image processing techniques that are well established. An area of exposed skin can be identified and isolated in each of the image frames of a video using, for example, object identification, pattern recognition, and facial recognition methods. A pixel classification method may also be used. Methods for classifying pixels in an image are disclosed in: "Determining A Total Number Of People In An IR Image Obtained Via An IR Imaging System", U.S. Pat. No. 8,520,074, which discloses a ratio method for classifying pixels in an image; "Determining A Number Of Objects In An IR Image", U.S. Pat. No. 8,587,657, which discloses a correlation method and a best fitting reflectance method for classifying pixels in an image; and "Determining A Pixel Classification Threshold For Vehicle Occupancy Detection", U.S. patent application Ser. No. 13/324,308, by Wang et al., which discloses a method for determining a threshold used for pixel classification, all of which are incorporated herein in their entirety by reference. Further, a technician may use a mouse or a touchscreen display to manually identify such areas during video capture or system setup and configuration. The identified areas would then be stored for use during video processing.

A "video segment" refers to a plurality of time-sequential image frames of the received video. Video segments do not have to be the same size.

A "next sequential video segment" refers to a plurality of image frames temporally subsequent to the image frames of the previous video segment.

"Identifying a video segment" during which a movement by the subject is or is not likely to have induced motion artifacts in the video can be effectuated using a plurality of techniques. For example, a motion detector can be utilized to provide a signal when the subject is moving or, alternatively, when the subject is not moving and the video segments associated with these time intervals can be readily identified. Motion of the subject being monitored can also be determined by a visual observation of a technician tasked with observing the subject during video acquisition. A software tool can be employed to continuously process streaming video to isolate areas of exposed skin in each image frame and to analyze those isolated areas for movement. Movement can be determined, for instance, by processing pixels in the isolated area of exposed skin in each of the image frames to determine an amount of change in center pixel locations associated with the area relative to a fixed object in the environment or a fixed position of the subject. A time interval where a movement occurred can be identified by a change in a shape of the area of exposed skin in the image frames, i.e., the head turned or an arm moved. In other embodiments, a facial recognition software or object tracking method is used. Software tools can be configured to send a signal, initiate an alert, or otherwise mark those time intervals when movement was or was not detected. A start/stop time facilitates identification of first video segments. A threshold for movement may be preset by a user or technician and, based upon the amount of movement, as detected in the image frames by image processing methods, relative to the pre-set threshold, time intervals associated with movement can be deemed to be significant enough to be identified accordingly or insignificant so as to be ignored. It should be appreciated that the types and kinds of movements likely to induce motion artifacts in the video will necessarily depend on the application wherein the teachings hereof find their intended uses. It is preferable that any motion by the subject be accounted for in the acquired video to obtain a more accurate physiological signal.

A "time-series signal" is a signal extracted from a video segment which contains meaningful data that relates to the desired physiological function for which the subject is being monitored. A time series signal is generated from a given video segment by processing pixels in the isolated areas of exposed skin in each of the image frames. One such method, for example, averages pixel values within an isolated area of exposed skin across the image frames in the video segment. For example, an average is computed of all pixels in each of the isolated areas within each image frame to obtain a channel average per frame. A global channel average is computed, for each channel, by adding the channel averages across multiple frames and dividing by the total number of frames. The channel average is subtracted from the global channel average and the result is divided by a global channel standard deviation to obtain a zero-mean unit variance time-series signal for that video segment. The time-series signal contains frequency components. The time-series signals may be normalized and are then subjected to a pre-filtering to remove undesirable frequencies. Individual time-series signal segments can be weighted as desired. Such a weighting may be applied over one or more segments while other signal segments are not weighted. Methods for weighting signal segments are widely understood in the signal processing arts. It should be appreciated that the time-series signal may be received or retrieved from a remote device such as a computer workstation over a wired or wireless network with the captured video having been communicated directly to the remote device for generation of the time-series signal on a continuous basis. The time-series signals extracted from the video segments are processed to extract a physiological signal.

A "physiological signal" is a signal that is extracted from a time-series signal and which corresponds to the physiological function for which the subject is being monitored. The following U.S. patent applications, which are incorporated in their entirety by reference, teach various aspects of extracting a physiological signal from a time-series signal generated from a video of a subject. "A Video Acquisition System And Method For Monitoring A Subject For A Desired Physiological Function", U.S. patent application Ser. No. 13/921,939, by Xu et al. "Processing Source Video For Real-Time Enhancement Of A Signal Of Interest", U.S. Pat. No. 8,879,867. "Filtering Source Video Data Via Independent Component Selection", U.S. Pat. No. 8,600,213. If camera related noise or other environmental factors affecting video capture are present, compensation can be introduced as described in: "Removing Environment Factors From Signals Generated From Video Images Captured For Biomedical Measurements", U.S. Pat. No. 9,185,353 , by Mestha et al. Physiological signals are stitched together to produce a continuous physiological signal for the subject.

"Stitching" refers to connecting segments of signals together to produce a continuous signal. Various embodiments of such stitching techniques are disclosed in: "Continuous Cardiac Pulse Rate Estimation From Multi-Channel Source Video Data", U.S. Pat. No. 8,855,384 by Survi Kyal et al. and "Continuous Cardiac Pulse Rate Estimation From Multi-Channel Source Video Data With Mid-Point Stitching", U.S. Pat. No. 9,036,877, by Survi Kyal et al. which are incorporated herein in their entirety by reference.

A "physiological function" refers to a respiratory or a cardiac function.

A "cardiac function" refers to a function of the cardiovascular system. In FIG. 1, assume patient 105 is being monitored for a cardiac function, i.e., the desired physiological function is a cardiac function and the target physiological signal is a cardiac signal. In this scenario, video imaging device 102 is capturing video of a first and second region, both in the camera's field of view $f_1$ at 109. The first region of interest is an area of the subject's chest where a cardiac signal can be registered by the video imaging device and the second region of interest is an area where a movement is likely to induce motion artifacts into the desired cardiac signal, i.e., a movement of the head area is likely to induce a movement in the chest area and a change in the cardiac function.

A "cardiac signal" is a signal obtained from having processed video of the subject. The cardiac signal is used for cardiac function assessment. Methods for extracting a cardiac signal from a time-series signal obtained from video are disclosed in the following U.S. patent applications which are incorporated herein in their entirety by reference. "Estimating Cardiac Pulse Recovery From Multi-Channel Source Data Via Constrained Source Separation", U.S. Pat. No. 8,617,081. "Deriving Arterial Pulse Transit Time From A Source Video Image", U.S. Pat. No. 8,838,209. "Video-Based Estimation Of Heart Rate Variability", U.S. Pat. No. 8,977,347. "Systems And Methods For Non-Contact Heart Rate Sensing", U.S. Pat. No. 9,020,185. "Continuous Cardiac Signal Generation From A Video Of A Subject Being Monitored For Cardiac Function", U.S. patent application Ser. No. 13/871,766, by Kyal et al. "Processing A Video For Vascular Pattern Detection And Cardiac Function Analysis", U.S. Pat. No. 8,897,522. "Subcutaneous Vein Pattern Detection Via Multi-Spectral IR Imaging In An Identity Verification System", U.S. Pat. No. 8,509,495. "Determining Cardiac Arrhythmia From A Video Of A Subject Being Monitored For Cardiac Function", U.S. Pat. No. 8,768,438. "Method And Apparatus For Monitoring A Subject For Atrial Fibrillation", U.S. patent application Ser. No. 13/937, 740, by Mestha et al. "Method And Apparatus For Monitoring A Subject For Fractional Blood Oxygen Saturation", U.S. patent application Ser. No. 13/937,949, by Mestha et al. "Method And Apparatus For Monitoring A Subject For Functional Blood Oxygen Saturation", U.S. patent application Ser. No. 13/937,782, by Mestha et al. "System And Method For Determining Video-Based Pulse Transit Time With Time-Series Signals", U.S. patent application Ser. No. 14/026,739, by Mestha et al.

A "respiratory function" refers to a function of the respiratory system.

A "respiratory signal" is a signal obtained from having processed video of the subject. The respiratory signal is used for respiratory function assessment. Methods for extracting a respiratory signal from a time-series signal obtained from video are disclosed in the following U.S. patent applications which are incorporated herein in their entirety by reference. "Monitoring Respiration with a Thermal Imaging System", U.S. Pat. No. 8,790,269. "Processing A Video For Tidal Chest Volume Estimation", U.S. Pat. No. 9,226,691, by Bernal et al. "Minute Ventilation Estimation Based On Depth Maps", U.S. Pat. No. 8,971,985. "Minute Ventilation Estimation Based On Chest Volume", U.S. patent application Ser. No. 13/486,715, by Bernal et al. "Processing A Video For Respiration Rate Estimation", U.S. patent application Ser. No. 13/529,648, by Bernal et al. "Respiratory Function Estimation From A 2D Monocular Video", U.S. Pat. No. 8,792,969. A system and method for generating flow-volume loops for respiratory function assessment is disclosed in: "Generating A Flow-Volume Loop For Respiratory Function Assessment", U.S. patent application Ser. No. 14/023,654, by Mestha et al.

A "frequency of interest" is a frequency obtained from signal that corresponds to the desired physiological function which can be used as a center frequency for the band-pass filter. It should be understood that the center frequency corresponds to the frequency at which the power spectral density of the signal is at a maximum.

"Analyzing a physiological signal" refers to identifying a frequency of interest $f_c$ in the physiological signal extracted from the time-series signal. The frequency of interest, in turn, is used to configure a center frequency of a band-pass filter.

A "band-pass filter" is an adaptive filter which can be dynamically configured to have a center frequency corresponding to the identified frequency of interest obtained from having analyzed a physiological signal. The band-pass filter has a pre-defined bandwidth $f_w$ where $f_c - f_w$ is the low cut-off frequency and $f_c + f_w$ is the higher cut-off frequency of the filter. It should be appreciated that the cut-off frequencies should be selected so that the filter has a bandwidth which retains desirable components of the respiratory or cardiac signal being filtered while rejecting undesirable components. In the case of monitoring adults for a cardiac function, a bandwidth of 0.2-0.3 Hz (change of 12-18 beats per minutes over a second) could be used. For infants, a wider bandwidth of 0.3-0.5 Hz (change of 18-30 bpm over a second) is preferred. For respiratory function assessment, the bandwidth will depend on the nature of the respiratory signal being extracted. It is to be noted that the approach is limited to respiratory state wherein subject's respiratory frequency is not changing rapidly. For example, during tidal breathing, change in respiratory frequency between each segment is not very high. Generally, in adults, during tidal breathing, the center frequency for tidal breathing is between 12 to 16 cycles per minute. A bandwidth of 2 to 4 cycles per minute around the center frequency is considered adequate. The reader is directed to the text: "Electronic Filter Design Handbook", Arthur Williams and Fred Taylor, McGraw-Hill Professional; 4th Ed. (2006), ISBN-13: 978-0071471718.

A "remote sensing environment" refers to non-contact, non-invasive sensing, i.e., the sensing device does not physically contact the subject being sensed. The sensing device can be any distance away from the subject, for example, as close as less than an inch to as far as miles in the case of telemedicine. The environment may be, for example, a hospital, ambulance, medical office, to name a few.

A "storage device" refers to a device or system for storing data, images, formulae, machine readable program instructions, and the like. Storage devices include RAM, ROM, Memory, CD-ROM, DVD, flash drives, hard drives, and other volatile or non-volatile media.

Example Video Acquisition System

Reference is now being made to FIG. 1 which illustrates an example system 100 for capturing a video of a subject of interest being monitored for a desired physiological signal in a non-contact, remote sensing environment in accordance with the teachings hereof.

In FIG. 1, video imaging device 102 is acquiring video of the patient 105 resting his head on a pillow while a lower portion of the subject's body is covered by a sheet. Technician 103 monitors the patient. Although the subject is shown in a prone position, it should be appreciated that video can be captured while the subject is in other positions such as sitting in a wheelchair or standing up. Video imaging device 102 is rotatably mounted on a robotic support arm 108 so the camera's field of view can be directed or re-directed to capture video of the first and second regions. The illustrated video imaging device captures time-sequential image frames of the subject using sensors which may be a single sensor or a sensor array including a plurality of individual or separate sensor units. A processor integral to the video imaging device receives video, processes the image frames in a manner as disclosed herein in real-time, and communicates signal(s) to display device 112 via antenna 110 or to one or more remote devices over network 101, such as the workstation of FIG. 6. The video imaging device may include wireless and wired elements and may be connected via other means such as coaxial cable, radio frequency, Bluetooth, or any other manner for communicating data. Monitor 112 is rotatably mounted to the support arm so the monitor can be turned as needed so others in the room can view video or signals 113 displayed thereon. The support arm is on wheels (not shown) so that the video imaging system can be moved from bed to bed and room to room throughout the facility. In various embodiments hereof, the subject's cardiac/respiratory signals are continuously displayed and monitored for the occurrence of a physiological event, and an alarm or notification initiated to a nurse, doctor, or technician in the event that the physiological function of the patient falls outside a set of pre-defined parameters.

Network 101 facilitates communication with remote devices such as, for instance, a workstation or a handheld device such as a Smartphone, iPhone, iPad, notebook, and the like. Data is transferred in the form of signals which may be, for example, electronic, electromagnetic, optical, light, or other signals. These signals are provided to a communications device such as a server which transmits and receives data packets by means of a wire, cable, fiber optic, phone line, cellular link, RF, satellite, or other medium or communication pathway. Techniques for placing devices in networked communication are well established. Therefore, a further discussion as to specific techniques for networking devices has been omitted. Any of the networked devices may include a network interface card or system.

Example Flow Diagram

Figure 2:
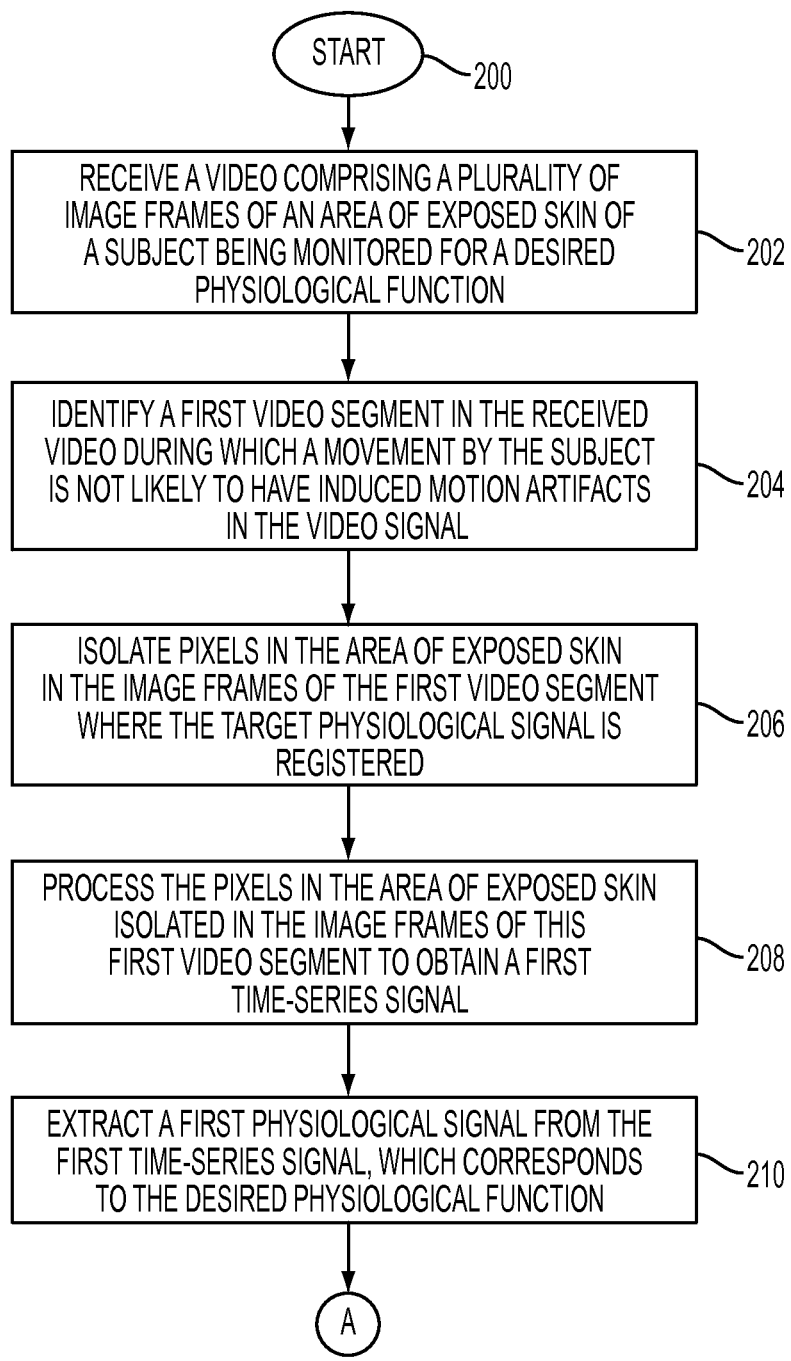
FIG. 2 illustrates one embodiment of the present method for compensating for motion induced artifacts in physiological signals generated from a video captured of a subject being monitored for a desired physiological function in accordance with the teachings hereof.

Reference is now being made to the flow diagram of FIG. 2 which illustrates one embodiment of the present method for compensating for motion induced artifacts in physiological signals obtained from a single video captured by a single video imaging device of a subject being monitored for a desired physiological function in a non-contact, remote sensing environment. Flow processing begins at step 200 and immediately proceeds to step 202.

At step 202, receive a video captured by a video imaging device of a first and second area of exposed skin of a subject being monitored for a desired physiological function. The video comprises a plurality of time-sequential image frames. The first area of exposed skin is where a signal corresponding to a desired physiological function can be registered. A second area is where a movement by the subject is likely to induce motion artifacts into the signal. In other embodiments, the video is of a single area of exposed skin and other means are employed, such as a motion sensor, to determine movement by the subject.

At step 204, identify a first video segment in the received video during which movement by the subject is not likely to have induced motion artifacts in the video signal. In one embodiment, technician 103 of FIG. 1 records the time interval when the patient did not move and the first video segment associated with that time interval is identified therefrom. In another embodiment, pixels of each frame of the streaming video are processed to isolate the first and second areas of exposed skin 106 and 107, respectively. In FIG. 1, the first area of exposed skin 106 is an area of the subject where a signal corresponding to the desired physiological function can be registered by the video imaging device. The second area of exposed skin 107 is an area of the subject where a movement by the subject is likely to induce motion artifacts into the signal intended to be extracted from the video. A time interval when the subject did not move can be determined from dynamically processing pixels in area 107 of the streaming video. The first video segment can be identified therefrom. Once the first video segment has been identified, processing continues with respect to step 206.

At step 206, isolate pixels in the area of exposed skin of the image frames of this first video segment where the target physiological signal is registered. In FIG. 1, the area of exposed skin is area 106 where a physiological signal corresponding to, for instance, a cardiac function can be registered by the video imaging device 102.

At step 208, process the pixels in the area of exposed skin isolated in the image frames of this first video segment to obtain a first time-series signal.

At step 210, extract a first physiological signal from the first time-series signal (obtained in step 208). The extracted physiological signal corresponds to the desired physiological function for which the subject is being monitored.

Figure 3:
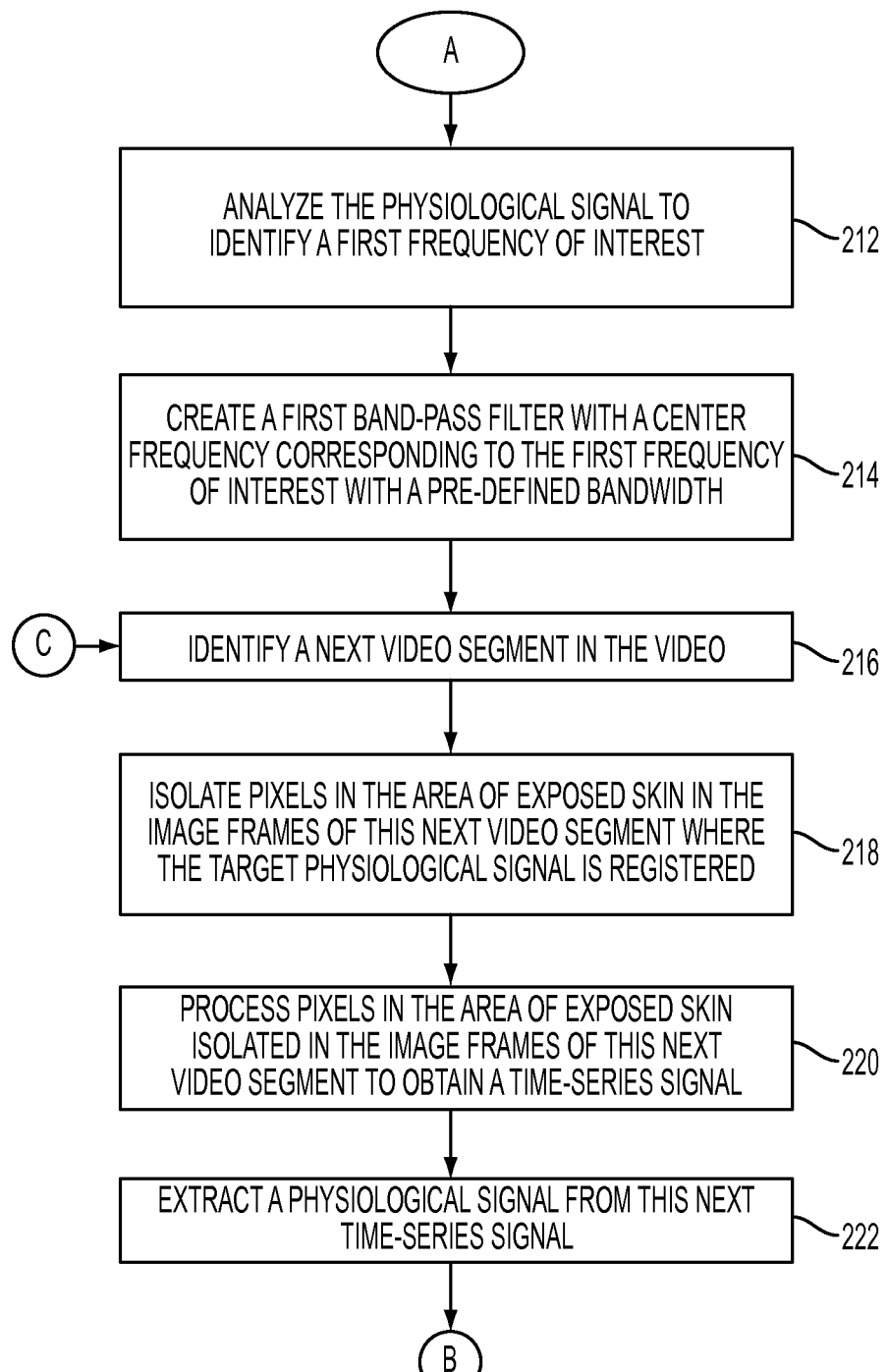
FIG. 3 is a continuation of the flow diagram of FIG. 2 with flow processing continuing with respect to node A.

Reference is now being made to FIG. 3 which is a continuation of the flow diagram of FIG. 2 with flow processing continuing with respect to node A.

At step 212, analyze the first physiological signal to identify a first frequency of interest.

At step 214, create a first band-pass filter corresponding to the frequency of interest (of step 212) with a pre-defined bandwidth.

At step 216, identify a next sequential video segment in the video.

At step 218, isolate pixels in the area of exposed skin of the image frames of this next video segment where the target physiological signal is registered.

At step 220, process pixels in the area of exposed skin isolated in the image frames of this next video segment (identified in step 216) to obtain a next time-series signal.

At step 222, extract a next physiological signal from the next time-series signal.

Figure 4:
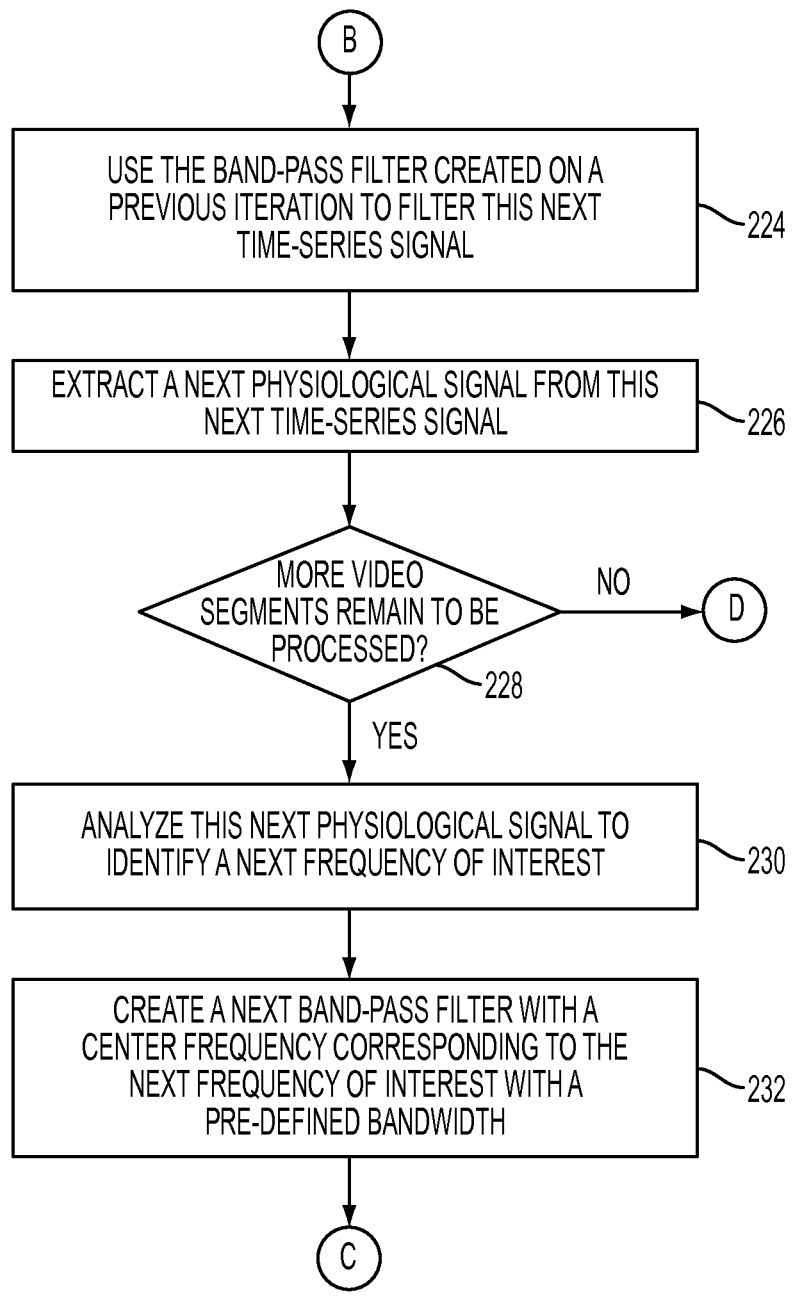
FIG. 4 is a continuation of the flow diagram of FIG. 3 with flow processing continuing with respect to node B.

Reference is now being made to FIG. 4 which is a continuation of the flow diagram of FIG. 3 with flow processing continuing with respect to node B.

At step 224, use the band-pass filter created on a previous iteration to filter this next time-series signal (of step 222). On a first iteration hereof, the first band-pass filter (created in step 214) is used to filter this next time-series signal. On a subsequent iteration, the next band-pass filter (created in step 232) is used to filter the subsequent next time-series signal. Filtering the next time-series signal produces a filtered time-series signal.

At step 226, extract a next physiological signal from the filtered time-series signal.

At step 228, a determination is made whether there are more video segments to process. If not then processing continues with respect to node D of FIG. 5. If there are more video segments remaining to be processed then processing continues with respect to step 230.

At step 230, analyze the next physiological signal to identify a next frequency of interest.

At step 232, create a first band-pass filter corresponding to the center frequency of interest with a pre-defined bandwidth. This next band-pass filter is used to filter a time-series signal on a next iteration. Flow processing then continues with respect to node C of FIG. 3 wherein, at step 216, a next sequential video segment is identified in the video for processing. Processing repeats for this next video segment until all video segments are processed accordingly. Once no further video segments are desired to be processed then processing continues with respect to step 234.

Figure 5:
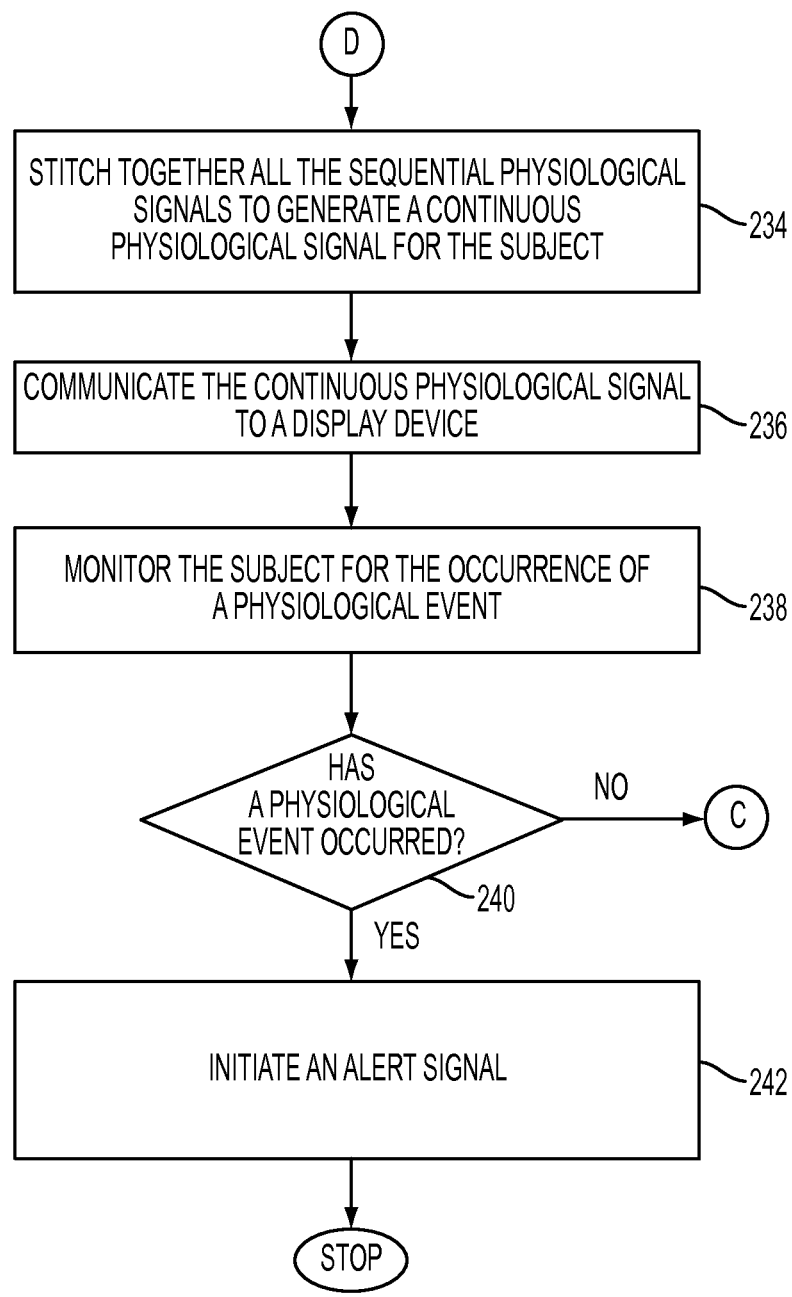
FIG. 5 is a continuation of the flow diagram of FIG. 4 with flow processing continuing with respect to node D.

Reference is now being made to FIG. 5 which is a continuation of the flow diagram of FIG. 4 with flow processing continuing with respect to node D.

At step 234, stitch all of the sequential physiological signals together to generate a continuous physiological signal for the subject. The sequential physiological signals may be stitched together in real-time as these signals are being extracted and filtered in the manner as disclosed herein. Such embodiments are intended to fall within the scope of the appended claims.

At step 236, communicate the continuous physiological information to a display device. One example device is shown at 112 in FIG. 1 displaying the continuous physiological signal 113 for the medical professional 103. The continuous physiological signal may be communicated to a storage device for storage and subsequent retrieval or communicated to a remote device over a network.

At step 238, monitor the subject for the occurrence of a physiological event. If the physiological function is a cardiac function and the continuous physiological signal is a cardiac signal then the subject would be monitored for the occurrence of any of: Cardiac Arrhythmia, Cardiac Stress, Cardiac Failure, and Heart Disease. If the physiological function is a respiratory function and the continuous physiological signal is a respiratory signal then the subject would be monitored for the occurrence of any of: Sudden Infant Death Syndrome, Respiratory Distress, Respiratory Failure, and Pulmonary Disease.

At step 240, a determination is made (as a result of the monitoring of step 238) whether a physiological event has occurred. If so then at step 242, initiate an alert signal. The alert signal or notification can be sent to a technician, nurse, medical practitioner, and the like. In one embodiment, the alert signal is communicated via network 101 of FIG. 1. Such a signal may take the form of a message or, for instance, a bell tone or a sonic alert being activated at a nurse's station. The alert signal may take the form of initiating a visible light which provides an indication such as, for instance, a blinking colored light. The alert can be a text, audio, and/or video message. Such embodiments are intended to be encompassed within the scope of the appended claims. Thereafter, in this embodiment further processing stops while additional actions are being taken in response to the alert signal. Alternatively, processing repeats with respect to node C. If no physiological event has occurred then processing repeats with respect to node C.

It should be appreciated that the teachings hereof are intended to be used in a continuous manner for patient monitoring wherein the first and second areas of exposed skin in the image frames of the video are continuously isolated and processed in real-time as video is being captured until the first video segment is identified where no movement has occurred. Thereafter, the first area of exposed skin is continuously isolated in each video segment and the extracted physiological signal extracted, filtered, and stitched together. If the subject moves, the steps of the present method can be repeated as needed with another first video segment being identified and subsequent next video segments processed accordingly.

The flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

Block Diagram of Processing System

Figure 6:
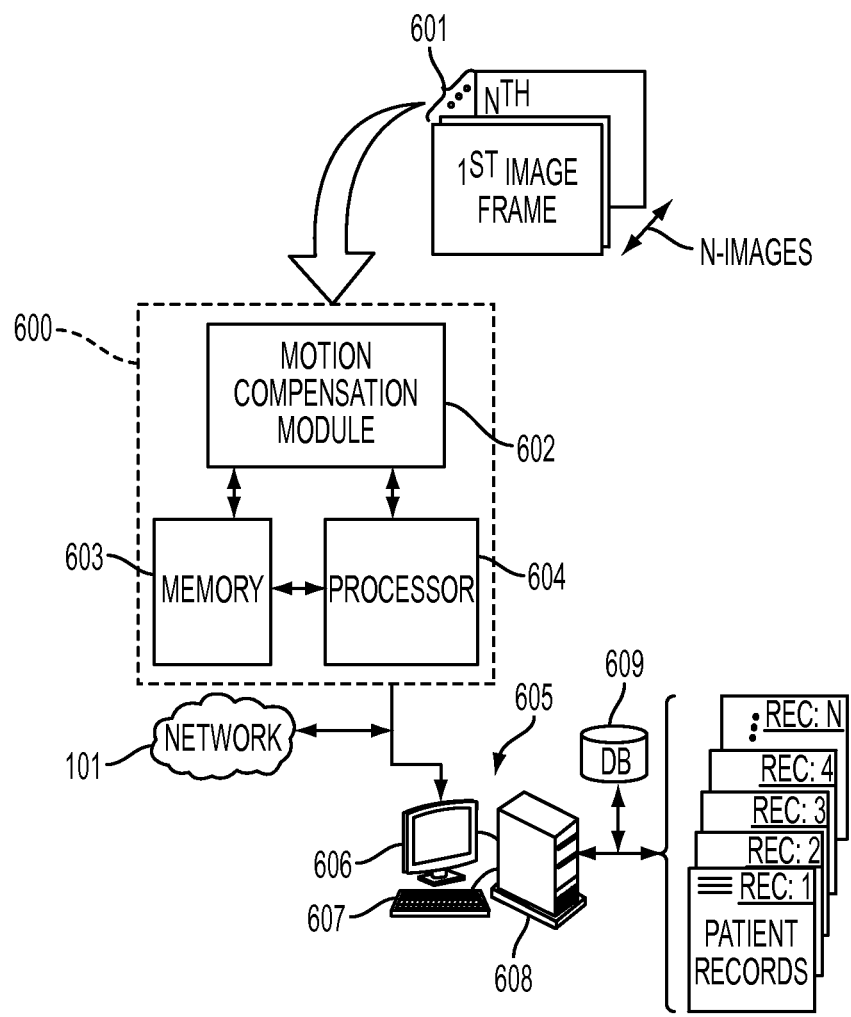
FIG. 6 shows a block diagram of one example video processing system 600 for processing a video in accordance with the embodiment shown and described with respect to the flow diagrams of FIGS. 2-5.

Reference is now being made to FIG. 6 which shows a block diagram of one example video processing system 600 for processing a video in accordance with the embodiment shown and described with respect to the flow diagrams of FIGS. 2-5.

A video imaging device captures video of a first and second area of exposed skin of a subject of interest being monitored for a desired physiological function, as shown and described with respect to the system of FIG. 1. The video comprises a plurality of time-sequential image frames, collectively at 601, which are received into a buffer (not shown) of the system 600. The time-sequential image frames may be communicated to storage device which can be, for instance, a hard drive, RAM, ROM, or a device with a removable media such as a DVD or CDROM drive. The received video may be pre-processed, as needed, for those video processing systems where it is desirable to first pre-process the received video in advance of further processing in accordance herewith. Video may be pre-processed, for example, to enhance contrast utilizing contrast enhancement techniques such as histogram equalization or contrast adjustment. Image frames can be skew and rotation corrected, if needed. Gaps detected between image frames in each of the x and y directions can be corrected, as desired. Various images can be boundary corrected and cropped and frame registration performed. Images can be pre-processed for relative shift due to the location of each filter band within the video and camera-to-object distance can also be corrected, where needed. Intensity values associated with pixels of images can be scaled based on a sensor response of each wavelength band of the video imaging systems. A weight can be also be applied.

In one embodiment, the pre-processed image frames are communicated to workstation 605 and displayed, for example, on display 606 such as a CRT, LCD, or touchscreen display. An alphanumeric keyboard 607 and a mouse effectuate a user input. Motion Compensation Module 602 receives video and, in cooperation with Memory 603 and Processor 604, performs the steps of the present method, as claimed. The continuous physiological signal generated by system 600 is communicated to the workstation shown comprising a computer case 608 housing a motherboard, CPU, memory, interface, storage device, and a communications link such as a network card. A user or technician may use the workstation to view the captured video in real-time and to dynamically enter values, identify a first video segment, select or enter a frequency of interest, select or enter parameters for the band-pass filter, select or otherwise identify areas of exposed skin within image frames for processing, and to post-process the continuous physiological signal such that the patient can be monitored for the desired physiological function.

It should be appreciated that the workstation has an operating system and other specialized software configured to display a variety of numeric values, text, scroll bars, pull-down menus with user selectable options, and the like, for entering, selecting, or modifying information. The workstation has a removable media 609 wherein patient records are stored. Although the database is shown as an external device, the database may be internal to the workstation mounted, for instance, on a hard drive housed therein. Records stored in the database can be indexed, searched, and retrieved in response to a query. Any of the information obtained or produced, including the image frames and signals generated and/or extracted by system 600 can be stored to patient records contained in the database and used for physiological function assessment and physiological event monitoring.

Any of the modules, memory and processor(s) of the system of FIG. 6 are in communication with the workstation via pathways (not shown) and may further be in communication with one or more remote devices over network 101 including video imaging device 102 via antenna 110. It should be appreciated that some or all of the functionality performed by the processing system 600 may be performed, in whole or in part, by components internal to the workstation. Moreover, the system 600 may additionally comprise one or more components which may, in turn, utilize software and hardware having a specialized processor for executing machine readable program instructions which facilitate performance of the intended function. The system 600 may further comprise an operating system, drivers, device controllers, and other apparatuses some or all of which may be connected via a network. One or more aspects of the present method may be implemented in conjunction with a smartphone.

Figure 7:
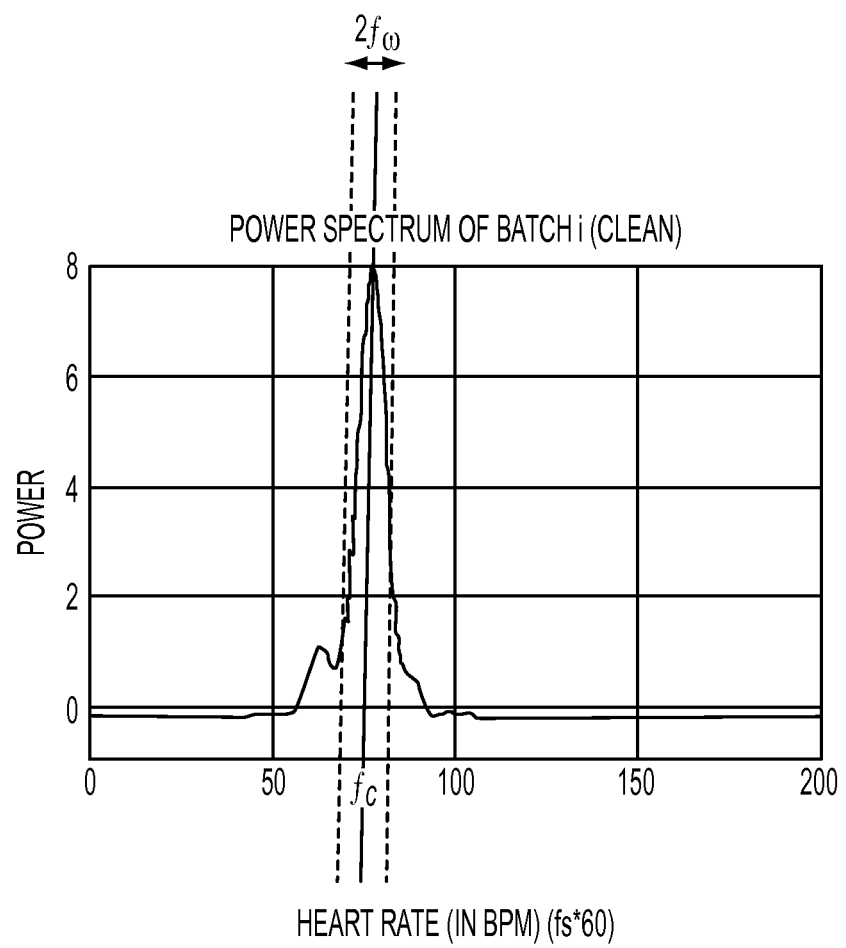
FIG. 7 shows a frequency of interest identified from a physiological signal extracted from a first video segment $S_i$, where i=1, in the received video during which movement by the subject was not likely to have induced motion artifacts in the video.

FIG. 7 shows a frequency of interest identified from a physiological signal extracted from a first video segment $S_i$, where i=1, in the received video during which movement by the subject was not likely to have induced motion artifacts in the video.

Figure 8:
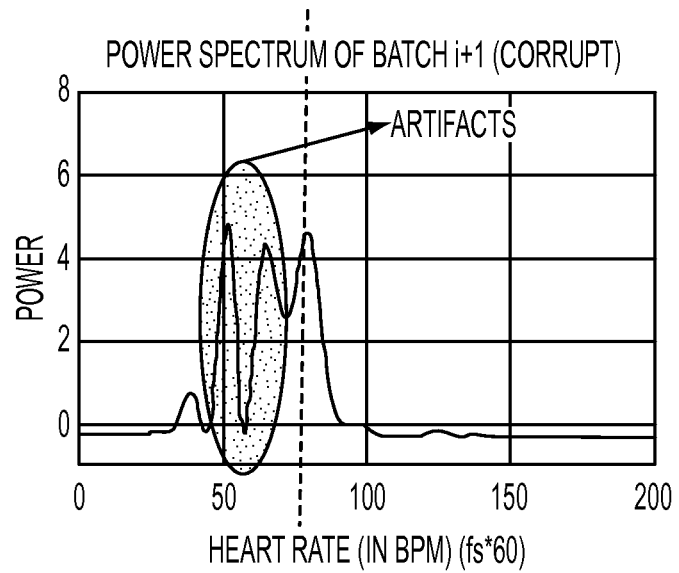
FIG. 8 shows a signal segment of a motion-corrupted physiological signal of a next video segment.

FIG. 8 shows a signal segment of a motion-corrupted physiological signal of a next video segment.

Figure 9:
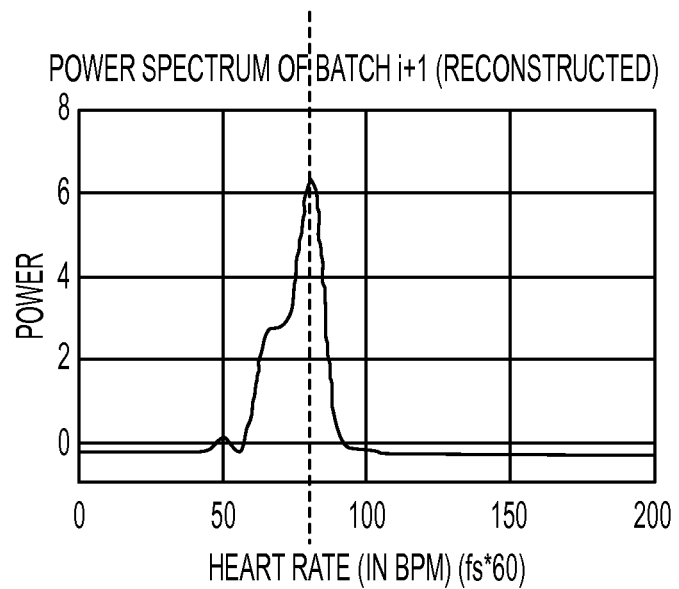
FIG. 9 shows the signal segment of FIG. 8 which has been processed for motion compensation using the teachings hereof which approximates the physiological signal of FIG. 7.

FIG. 9 shows the signal segment of FIG. 8 which has been processed for motion compensation using the teachings hereof. Note that it approximates the "clean" physiological signal of FIG. 7.

Various aspects of the teachings hereof may be practiced in distributed computing environments where tasks are performed by a plurality of devices linked via a network. The teachings hereof may be partially or fully implemented in software using source code that can be used on a variety of computer platforms. One or more of the capabilities hereof can be emulated in a virtual environment or leverage off-the-shelf software. The teachings hereof can be implemented using any known or later developed systems, structures, devices, or software by those skilled in the applicable art without undue experimentation from the description provided herein.

One or more aspects of the systems and methods described herein are intended to be incorporated in an article of manufacture. The article of manufacture may be shipped, sold, leased, or otherwise provided separately either alone or as part of an add-on, update, upgrade, or product suite. Various of the above-disclosed features and functions, or alternatives thereof, may be combined into other systems or applications. Presently unforeseen or unanticipated alternatives, modifications, variations, or improvements may become apparent and/or subsequently made by those skilled in the art which are also intended to be encompassed by the following claims. It will be appreciated that the above-disclosed and other features and functions, or alternatives thereof, may be desirably combined into many other different systems or applications. Changes to the above-described embodiments may be made without departing from the spirit and scope of the invention. Any printed publications including patents and patent applications are each separately hereby incorporated by reference in their entirety.

What is claimed is:

1. A method for compensating for motion induced artifacts in physiological signals extracted from video captured of a subject being monitored for a physiological function in a non-contact, remote sensing environment, the method comprising:

receiving a video comprising a plurality of time-sequential image frames captured by a video imaging device of a subject being monitored for a desired physiological function, said image frames containing at least one area of exposed skin where a signal corresponding to said physiological function can be registered by said video imaging device;

identifying a first video segment $S_i$, where i=1, in said received video during which movement by said subject is not likely to have induced motion artifacts in the video;

processing pixels in image frames of said first video segment to obtain a first time-series signal;

extracting, from said first time-series signal, a first physiological signal corresponding to said physiological function;

analyzing said first physiological signal to identify a first frequency of interest $f_{c_i}$;

creating a first band-pass filter with a center frequency $f_{c_i}$ and a bandwidth $f_{w_i}$; and repeating for all next sequential video segments $S_{i+1}$ in said received video:

processing pixels in image frames of said next video segment to obtain a next time-series signal;

dividing said next time-series signal into batches for processing, with successive batches having at least a 95% overlap with a previous batch;

extracting, from said next time-series signal, a next physiological signal;

using the created band-pass filter to filter said next time-series signal; wherein on a first iteration of said repeating, the created first band-pass filter is used and on subsequent iterations of said repeating, a next band-pass filter is used;

extracting, from said filtered next time-series signal, a next physiological signal corresponding to said physiological function;

analyzing said next physiological signal to identify a next frequency of interest $f_{c_{i+1}}$; and creating the next band-pass filter having a center frequency $f_{c_{i+1}}$ and a bandwidth $f_{w_{i+1}}$ to be used to filter a time-series signal on a next iteration;

stitching all of said extracted physiological signals together to generate a continuous physiological signal for said subject, said stitching comprising mid-point stitching; and using said continuous physiological signal to monitor said subject for said desired physiological function.

2. The method of claim 1, wherein a bandwidth of said band-pass filters is based upon a rate of change of a heart rate of an age group belonging to said subject.

3. The method of claim 1, wherein said video imaging device is any of: a RGB video camera, a 3D video camera, an infrared video camera, a multi-spectral video camera, a hyperspectral video camera, or a hybrid camera comprising any combination hereof.

4. The method of claim 1, wherein identifying a video segment during which a movement by said subject is not likely to have induced motion artifacts in said video comprises any of: a motion detector providing a signal when said subject is moving or not moving, or visually observing said subject.

5. The method of claim 1, wherein said processed pixels of image frames of a given video segment are associated with said area of exposed skin.

6. The method of claim 5, wherein said area of exposed skin is isolated in said image frames using any of: pixel classification, object identification, facial recognition, color, texture, spatial features, spectral information, pattern recognition, or a user input.

7. The method of claim 1, wherein said physiological function is a cardiac function, and said continuous physiological signal is a cardiac signal, further comprising analyzing said cardiac signal to determine any of: heart rate variability, cardiac pulse frequency, or pulse transit time.

8. The method of claim 7, further comprising using said cardiac signal to determine a condition related to any of: Cardiac Arrhythmia, Cardiac Stress, Cardiac Failure, or Heart Disease.

9. The method of claim 1, wherein said physiological function is a respiratory function and said continuous physiological signal is a respiratory signal, further comprising analyzing said respiratory signal to determine any of: pulmonary volumes, minute ventilation, flow-volume loops, breathing pattern, and respiration rate.

10. The method of claim 9, further comprising using said respiratory signal to determine a condition related to any of: Sudden Infant Death Syndrome, respiratory distress, respiratory failure, or pulmonary disease.

11. The method of claim 1, wherein said video is a live streaming video and said continuous physiological signal is generated in real-time.

12. The method of claim 1, further comprising, in advance of filtering, detrending said time-series signal to remove low frequency variations and non-stationary components.

13. A system for compensating for motion induced artifacts in physiological signals extracted from video captured of a subject being monitored for a physiological function in a non-contact, remote sensing environment, the system comprising:
- a storage device; and
- a processor in communication with said storage device, said processor executing machine readable program instructions for:
  - receiving a video comprising a plurality of time-sequential image frames captured by a video imaging device of a subject being monitored for a desired physiological function, said image frames containing at least one area of exposed skin where a signal corresponding to said physiological function can be registered by said video imaging device;
  - identifying a first video segment $S_i$, where i=1, in said received video during which movement by said subject is not likely to have induced motion artifacts in the video;
  - processing pixels in image frames of said first video segment to obtain a first time-series signal;
  - extracting, from said first time-series signal, a first physiological signal corresponding to said physiological function;
  - analyzing said first physiological signal to identify a first frequency of interest $f_{c_i}$;
  - creating a band-pass filter with a center frequency $f_{c_i}$ and a bandwidth $f_{w_i}$; and
  - repeating for all next sequential video segments $S_{i+1}$, in said received video:
    - processing pixels in image frames of said next video segment to obtain a next time-series signal;
    - dividing said next time-series signal into batches for processing, with successive batches having at least a 95% overlap with a previous batch;
    - extracting, from said next time-series signal, a next physiological signal;
    - using the created the band-pass filter to filter said next time-series signal; wherein on a first iteration of said repeating, the created first band-pass filter is used and on subsequent iterations of said repeating, a next band-pass filter is used;
    - extracting, from said filtered next time-series signal, a next physiological signal corresponding to said physiological function;
    - analyzing said next physiological signal to identify a next frequency of interest $f_{c_{i+1}}$; and
    - creating the next band-pass filter having a center frequency $f_{c_{i+1}}$ and a bandwidth $f_{w_{i+1}}$ to be used to filter a time-series signal on a next iterations;
  - stitching all of said extracted physiological signals together to generate a continuous physiological signal for said subject, said stitching comprising a mid-point stitching; and
  - using said continuous physiological signal to monitor said subject for said desired physiological function.

14. The system of claim 13, wherein a bandwidth of said band-pass filters is based upon a rate of change of a heart rate of an age group belonging to said subject.

15. The system of claim 13, wherein said video imaging device is any of: a RGB video camera, a 3D video camera, an infrared video camera, a multi-spectral video camera, a hyperspectral video camera, or a hybrid camera comprising any combination hereof.

16. The system of claim 13, wherein identifying a video segment during which a movement by said subject is not likely to have induced motion artifacts in said video comprises any of: a motion detector providing a signal when said subject is moving or not moving, or visually observing said subject.

17. The system of claim 13, wherein said processed pixels of image frames of a given video segment are associated with said area of exposed skin.

18. The system of claim 17, wherein said area of exposed skin is isolated in said image frames using any of: pixel classification, object identification, facial recognition, color, texture, spatial features, spectral information, pattern recognition, or a user input.

19. The system of claim 13, wherein said physiological function is a cardiac function, and said continuous physiological signal is a cardiac signal, further comprising analyzing said cardiac signal to determine any of: heart rate variability, cardiac pulse frequency, or pulse transit time.

20. The system of claim 19, further comprising using said cardiac signal to determine a condition related to any of: Cardiac Arrhythmia, Cardiac Stress, Cardiac Failure, or Heart Disease.

21. The system of claim 13, wherein said physiological function is a respiratory function and said continuous physiological signal is a respiratory signal, further comprising analyzing said respiratory signal to determine any of: pulmonary volumes, minute ventilation, flow-volume loops, breathing pattern, or respiration rate.

22. The system of claim 21, further comprising using said respiratory signal to determine a condition related to any of: Sudden Infant Death Syndrome, respiratory distress, respiratory failure, or pulmonary disease.

23. The system of claim 13, wherein said video is a live streaming video and said continuous physiological signal is generated in real-time.

24. The system of claim 13, further comprising, in advance of filtering, detrending said time-series signal to remove low frequency variations and non-stationary components.

* * * * *